United States Patent [19]

Fox

[11] Patent Number: 5,410,474
[45] Date of Patent: Apr. 25, 1995

[54] BUTTONLESS MEMORY SYSTEM FOR AN ELECTRONIC MEASUREMENT DEVICE

[75] Inventor: David Fox, Mishawaka, Ind.
[73] Assignee: Miles Inc., Elkhart, Ind.
[21] Appl. No.: 97,477
[22] Filed: Jul. 27, 1993
[51] Int. Cl.$^6$ .......................... G06F 15/00; A61B 5/00
[52] U.S. Cl. .............................. 364/413.07; 128/637; 364/413.02; 364/413.08; 364/413.09
[58] Field of Search ...................... 364/413.01, 413.02, 364/413.03, 413.07, 413.08, 413.09; 128/770, 771, 637

[56] References Cited

U.S. PATENT DOCUMENTS 4,637,403  1/1987  Garcia et al. ...................... 128/770

Primary Examiner—Gail O. Hayes
Assistant Examiner—Stephen R. Tkacs
Attorney, Agent, or Firm—Roger N. Coe

[57] ABSTRACT

The buttonless memory system of the present invention retrieves and stores the measurement results of a sample for the user of an electronic measurement device, particularly a portable and personal electrical measurement device, with minimal user interaction. The user simply activates the portable measurement device and waits as the buttonless memory system initially cycles through the stored measurement results. The buttonless memory system stops retrieving from memory when the measurement device detects a sample or control solution. After test measurement of the sample, the user can choose to store the measurement result by deactivating the measurement device during the time the memory display is on. If the sample is a control solution, the user can delete the measurement result from memory by waiting and deactivating the measurement device after the memory display is off. In this way, the buttonless memory system provides a simple and effective memory management scheme for measurement devices.

17 Claims, 5 Drawing Sheets

BUTTONLESS MEMORY SYSTEM FOR AN ELECTRONIC MEASUREMENT DEVICE

BACKGROUND OF THE INVENTION

A. Field of the Invention

The present invention generally relates to a memory feature accessible without the need for any buttons (i.e., buttonless memory) used in an electronic measurement device for analyzing a sample. More particularly, the present invention relates to a buttonless memory system for retrieving, displaying and storing measurement results obtained by the electronic measurement device that is characterized as a personal and portable measurement device.

B. Description of the Background Art

Today, electronic instruments are more compact, more reliable and more user friendly than older electrical instruments. Present electronic instruments accurately perform a multitude of functions and are portable due to their compactness. These portable electronic instruments are carried by the user or conveniently kept at the user's home or office. Compactness, reliability and ease of use are especially important features for a portable electrical instrument that performs medical measurements, such as a blood/glucose meter.

Diabetics use blood/glucose meters to monitor the sugar level in their blood. Diabetics carry these compact and portable blood/glucose meters to periodically and conveniently monitor their blood/sugar level. Several types of portable blood/glucose meters exist.

Reflectance photometers determine the sugar level of a blood sample through color development. The user places a drop of blood onto a chemically treated test strip. The test strip changes color depending on the sugar concentration of the blood. The user then inserts the test strip into the reflectance photometer, and light from a light-emitting diode is reflected onto the colored test strip. Reflected light normally passes through a wavelength filter and strikes a photodetector. The electrical signals from the photodetector are evaluated and the sugar concentration of the blood sample is determined and displayed by the reflectance photometer. Some reflectance photometers also include memory for storing previous measurement results, but the memory feature is dependent upon human direction. As such, the memory feature is not always used effectively. The memory feature is important because many users, such as diabetics, must keep track of their measurement results.

These users, however, must affirmatively perform the additional function of retrieving stored measurement results from memory. In a typical reflectance photometer, the user must repeatedly press a button in order to review previous measurement results stored in memory. Unfortunately, many users have difficulty in reviewing previous measurement results stored in memory because they are intimidated by electronic instruments. In addition, the likelihood of human error degrading measurement results increases as the responsibility on the user increases. Therefore, simplicity is an important characteristic for a portable electrical measurement device for analyzing personal samples.

Another known blood/glucose meter operates using an electrode sensor technology. The user inserts a test sensor into a test slot, activating the meter. Upon activation, this blood/glucose meter using electrode sensor technology displays a calibration code and the last test result. The blood/glucose meter automatically stores the last measurement result and does not allow the user to decide whether to store a measurement result or not because this portable electrode sensor lacks memory management capability.

This blood/glucose meter continues the above display until a sample is detected at a test end of the test sensor. In use, the test end of the test sensor contacts a drop of a blood sample and, through capillary action, draws a small amount of blood into a test sensor reaction chamber housing a reagent-covered electrode. Glucose in the sample reacts with reagents on the electrode of the test sensor, and the reaction produces a current which is proportional to the glucose in the blood sample. The blood/glucose meter derives the glucose concentration from this reaction current and, after 60 seconds, displays the glucose concentration of the blood sample. Removing the test sensor deactivates the blood/glucose meter and the final measurement result is automatically stored.

This portable blood/glucose meter is simple because it automatically stores the last measurement result, but the effectiveness of this memory capability is questionable due to the lack of memory management capabilities. The last test result can simply be a control test result. The control test result is important to ascertain the accuracy of the meter but does not represent the user's actual blood/glucose level. Additionally, previous measurement devices such as the reflectance photometers described above possess memory management capabilities but require additional affirmative acts from the user such as pressing a button or switch at the right time or pressing and holding a button in order to accurately retrieve and store measurement results. The more actions the user must perform, the more likely human error can adversely affect the storing and monitoring of measurement results. Thus, it is advantageous to make blood/glucose meters or any other portable electrical measurement devices with memory management capabilities as simple as possible by not requiring the user to affirmatively perform the functions of storing and retrieving measurement results from memory.

SUMMARY OF THE INVENTION

The present invention provides a buttonless memory system for an electrical measurement device that requires a minimum amount of human interaction for the performance of memory management features, such as the storage and retrieval of measurement results. The buttonless memory system performs a memory management feature during a corresponding time period for that memory management feature. The user of the buttonless memory system simply waits for the appropriate time when the buttonless memory system indicates the performance of the desired memory management feature. The user is not required to press any buttons or switches to perform a desired memory management feature.

The buttonless memory system includes a processor that retrieves previous measurement results from a memory capable of storing the measurement results, other measurement information and operation instructions. While retrieving the measurement results and any additional information, the processor displays these measurement results and any additional information on a display of the electrical measurement device during a first time period after the activation of the electrical measurement device. The buttonless memory system can include voice-activated circuitry responsive to voice commands, and the first time period can commence after the issuance of a proper voice command. The processor displays the previous measurement results on the display during the first time period and signals the user that the results being displayed are the previous measurement results stored in memory. Alternatively, the processor can activate a memory indicator during the first time period to signal the user regarding the memory retrieval operations. After the first time period ends, the electrical measurement device stops displaying the previous measurement results and any additional information. The first time period ends upon either the expiration of a predetermined time interval, the receiving of a sample for measurement by the electrical measurement device or the issuance of a voice command to that effect.

Additionally, the memory system of the present invention stores measurement results with minimum human interaction. The memory system of the present invention automatically stores a current measurement result for a second time period or after the issuance of a proper voice command. At that time, the processor stores the measurement result in memory and informs the user that the current measurement result is stored in memory and remains stored in memory even if the electrical measurement device is deactivated. Alternatively, the processor activates the memory indicator to signal a stored measurement result. After the second time period ends or after the issuance of another proper voice command, the processor discards the current measurement result from memory and displays a message informing the user that the current measurement result is not in memory, or alternatively, deactivates the memory indicator. Deactivation of the memory indicator after the second time period indicates that the current measurement result is not stored in memory. In this way, users of these electrical measurement devices can conveniently review and store measurement results with no additional effort, improving the user's awareness of their physical condition as well as reducing degradation of measurement results due to human error.

In a preferred embodiment of the present invention, the electrical measurement device is a blood/glucose meter using the electrode sensor technology previously described. A user inserts a test sensor into a test slot of the blood/glucose meter, activating the blood/glucose meter. The meter displays an initial display until a blood sample is detected at a test end of the test sensor or a predetermined time interval has passed. After the initial display, a buttonless memory system or processor of the blood/glucose meter automatically retrieves previous measurement results from the memory and displays them on the display of the blood/glucose meter for a first time period. The first time period lasts for a predetermined time interval, until the blood/glucose meter detects a blood sample, or until a voice command is given if the buttonless memory system is voice-activated. During this first time period, the processor also indicates with a memory message on the display that previous measurement results from memory are on the display, or alternatively, the processor activates a memory indicator to inform the user that previous measurement results from memory are on the display. Upon detecting a blood sample, the processor halts the retrieving and displaying of measurement results and begins a testing or measurement sequence during which time the blood/glucose meter calculates the glucose concentration in the blood sample.

After determining the glucose concentration of the blood sample, the blood/glucose meter displays the current measurement result along with a message on the display indicating that the buttonless memory system has stored the measurement result in memory for a second time period. Alternatively, the blood/glucose meter displays the current measurement result and activates the memory indicator. The memory indicator indicates that the buttonless memory has stored the measurement result in memory in case the blood/glucose meter is deactivated. After the second time period has passed, the blood/glucose meter continues to display the current measurement result for a third time period but with a proper message on the display informing the user that the current measurement result is deleted from memory. The blood/glucose meter could also display the current measurement device with the memory indicator deactivated for the third time period. The absence of the memory indicator signals the user that the current measurement result is deleted from memory if the blood/glucose meter is deactivated during the third time period. Finally, the buttonless memory system stores the current measurement result in memory after the third time period has passed and while the blood/glucose meter remains on.

The buttonless memory system of the present invention makes it extremely convenient for users of electrical measurement devices to monitor previous measurement results stored in memory. Additionally, the buttonless memory system provides the ability to manage the storing of current measurement results in memory. The present invention stores a current measurement result in memory if the measurement device is deactivated during a first time period. If the user does not want to store the measurement result in memory or wants to activate a different memory management feature, the user just waits until the appropriate time to turn off the measurement device. The present invention only requires the user to observe the measurement device for an indication of the memory management feature being performed during that time period. Alternatively, voice-activated commands can expedite the operation of the buttonless memory system by eliminating any waiting and further simplify the memory management capability of the buttonless memory system. Thus, the buttonless memory system for an electronic measurement device provides effective memory management and display of previous measurement results while simplifying and reducing the amount of human interaction required for managing the memory of the measurement device.

BRIEF DESCRIPTION OF THE DRAWINGS

The advantages of the present invention will become apparent upon reading the following detailed description and upon reference to the accompanying drawings in which.

DETAILED DESCRIPTION OF THE PREFERRED EMBODIMENT

Figure 1:
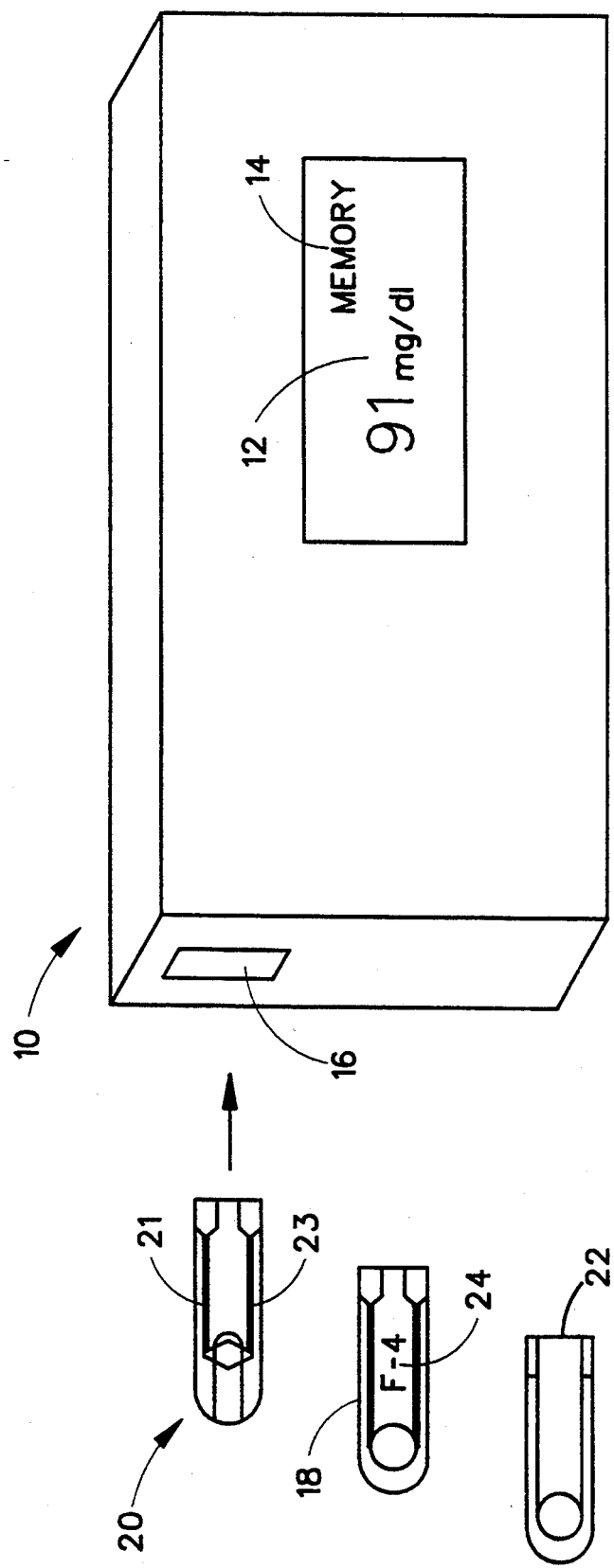
FIG. 1 is a perspective view of an electrical measurement device that includes the buttonless memory system of the present invention.

Referring now to the drawings, and more particularly to FIG. 1, there is illustrated an electrical measurement device, generally designated by reference numeral 10. The electronic measurement device 10 is characterized as a portable electronic measurement device for analyzing a personal sample, such as a blood sample from the user. The measurement device 10 analyzes a sample (not shown), obtains a measurement result for the sample depending on the analysis and displays the measurement result on a display 12. For example, if the measurement device 10 is a blood/glucose meter, the measurement result can be the level of glucose in the user's blood sample. Obviously, the measurement device 10 can be used to determine the presence and/or amount of other analytes in body fluids.

The measurement device 10 includes a processor (not shown) and a memory (not shown) capable of storing measurement results, other measurement information and operation instructions. The memory for the measurement device 10 preferably includes a ROM for storing the operation instructions and a RAM for storing measurement results and any additional information. The additional information can include time of measurement information, such as the time and date of each measurement result or the amount of time between measurement results, or additional information derived from the previous measurement results in memory, such as the average of the previous measurement results in memory.

The buttonless memory system of the present invention improves the memory utilization of the electrical measurement device 10 and also enhances the actual monitoring of the previous measurement results for a user of the device 10. The buttonless memory system accomplishes this by minimizing the amount of human interaction required for managing the memory of the measurement device 10. The buttonless memory system relies on timing and a visual prompt or a memory indicator 14 to signal the user that a memory management feature is being performed, such as a previously stored measurement results being displayed or a current measurement result is stored in memory. The memory indicator 14 can be replaced by displaying memory management prompts or messages on the display 12.

For retrieving previous measurement results from memory, a user simply activates the measurement device 10 and waits as the buttonless memory system cycles through memory for a first time period while the memory indicator 14 is on. The user can bypass the retrieval of measurement results by simply commencing with the current measurement. After the analysis of the sample, the user can choose to store the result by simply deactivating the measurement device 10 while the memory indicator 14 is on. The buttonless memory system can include voice-activation circuitry (not shown) to expedite and activate the memory management capabilities of the buttonless memory system at any time.

Figure 2:
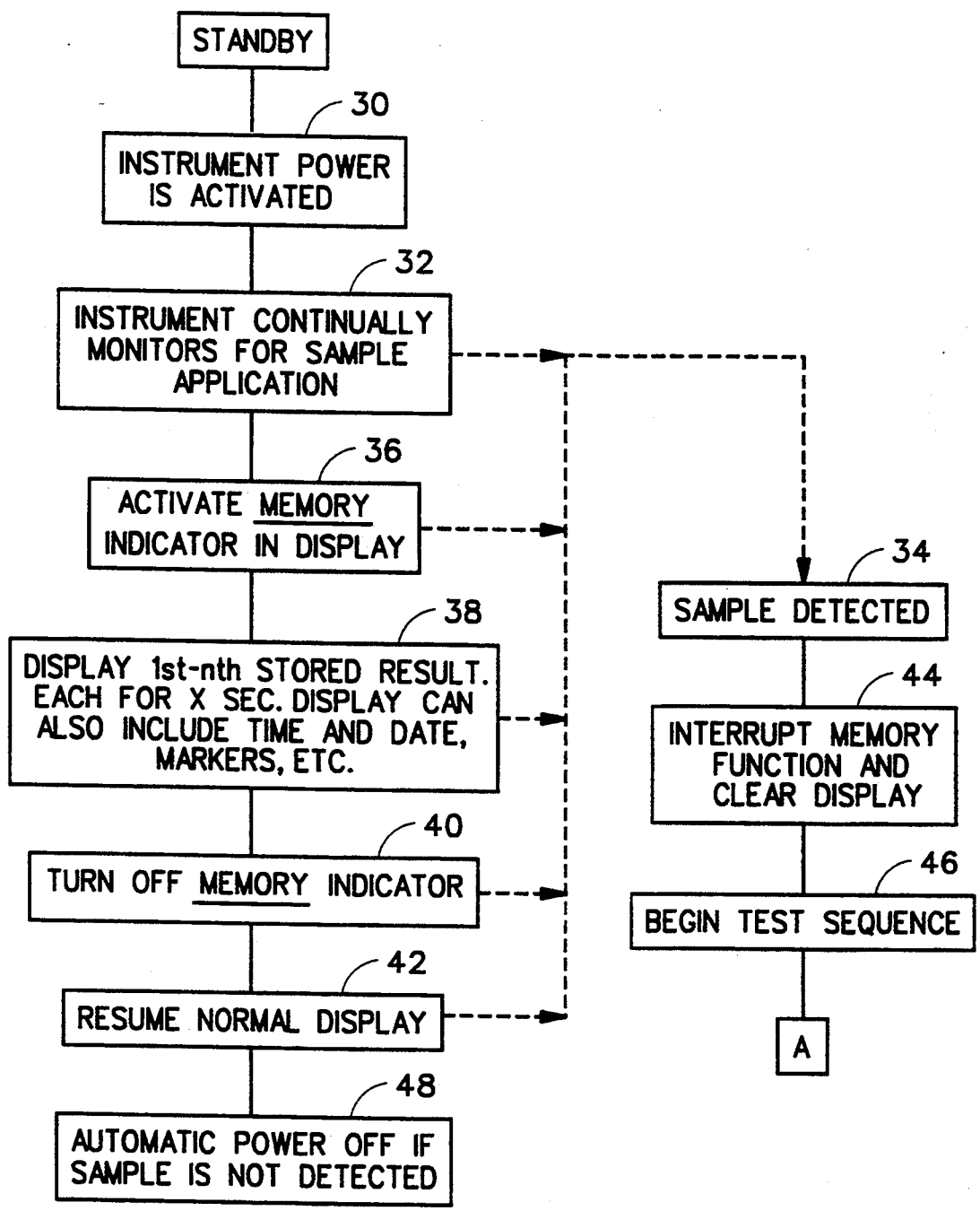
FIG. 2 illustrates a flow chart diagram detailing the retrieval of measurement results from memory by the buttonless memory system of the present invention.

FIG. 2 illustrates a flow diagram of the retrieval of measurement results from memory according to the buttonless memory system operating within the electrical measurement device 10. After the measurement device 10 is activated at step 30, the measurement device 10 continually monitors for the application of a measurement sample at step 32. Until step 34 detects a sample, step 36 activates the memory indicator 14. As illustrated, the memory indicator 14 is in the display 12. At this time, the memory indicator 14 signals the user that previous measurement results stored in memory are being displayed. Step 38 cycles through the N measurement results in memory and displays each previous measurement result, along with other information such as time and date markers, for X seconds.

After the buttonless memory system has cycled through the stored measurement results, step 40 turns off the memory indicator 14, and step 42 resumes the normal display on the display 12. If step 34 does detect a sample, then step 44 immediately interrupts any one of the steps 32, 36, 38, 40 or 42 of the buttonless memory system and clears the display 12, and step 46 initiates the measuring of the sample. If step 34 does not detect a sample after the memory indicator 14 has been turned off at step 40, then step 48 automatically deactivates the measurement device 10 after a predetermined time interval.

Figure 3:
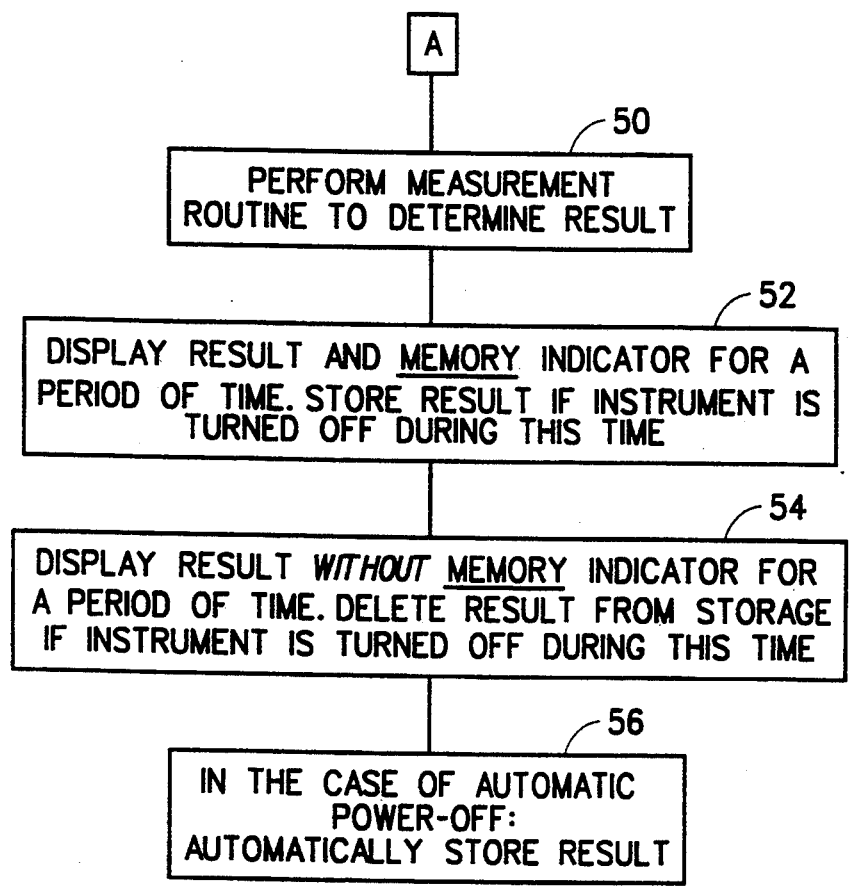
FIG. 3 illustrates a flow chart diagram detailing the storage of measurement results into memory by the buttonless memory system of the present invention.

FIG. 3 shows the sequence followed by the buttonless memory system for storing a measurement result in memory. At step 50, the measurement device 10 performs a measurement routine to determine a current measurement result for the sample. Step 52 displays the current measurement result and activates the memory indicator 14 on the display 12 for a second time period. In this case, the memory indicator 14 indicates to the user that the current measurement result is stored in the memory of the measurement device 10, and if the device 10 is turned off during this time, the current measurement result remains stored in memory.

After the second time period, step 54 displays the result on the display 12 without the memory indicator 14 for a third time period. The absence of the memory indicator 14 informs the user that the current measurement result has been deleted from memory, and if the measurement device 10 is turned off during this time, the current measurement result is not stored in memory. Moreover, if the device 10 automatically turns off after the third time period, step 56 ensures that the current measurement result is stored in memory.

In a preferred embodiment of the present invention, the electrical measurement device 10 of FIG. 1 is a portable blood/glucose meter using electrode sensor technology. This measurement device 10 lacks any buttons, knobs or user-controlled switches. The measurement device 10 does include a test slot 16 for receiving a code sensor 18, a test sensor 20 or a check sensor 22 which activate the measurement device 10 upon insertion into the test slot 16. Initially, a user must calibrate the meter 10 by using the code sensor 18 corresponding to the current test sensor 20. Each lot of test sensors 20 is tested extensively and assigned a function number 24 identified on the code sensor 18 provided with each lot. By inserting the code sensor 18 into the test slot 16, the user calibrates or matches the meter 10 to the reactivity of the corresponding test sensor 20. After calibration, the function number 24 (shown as F-4 in FIG. 1) appears in a display 12 of the meter 10, and the user removes the code sensor 18, deactivating the meter 10. The user can test the accuracy of the meter by inserting the check sensor 22 or inserting the test sensor 20 and performing a measurement on a control sample (not shown).

Figure 4:
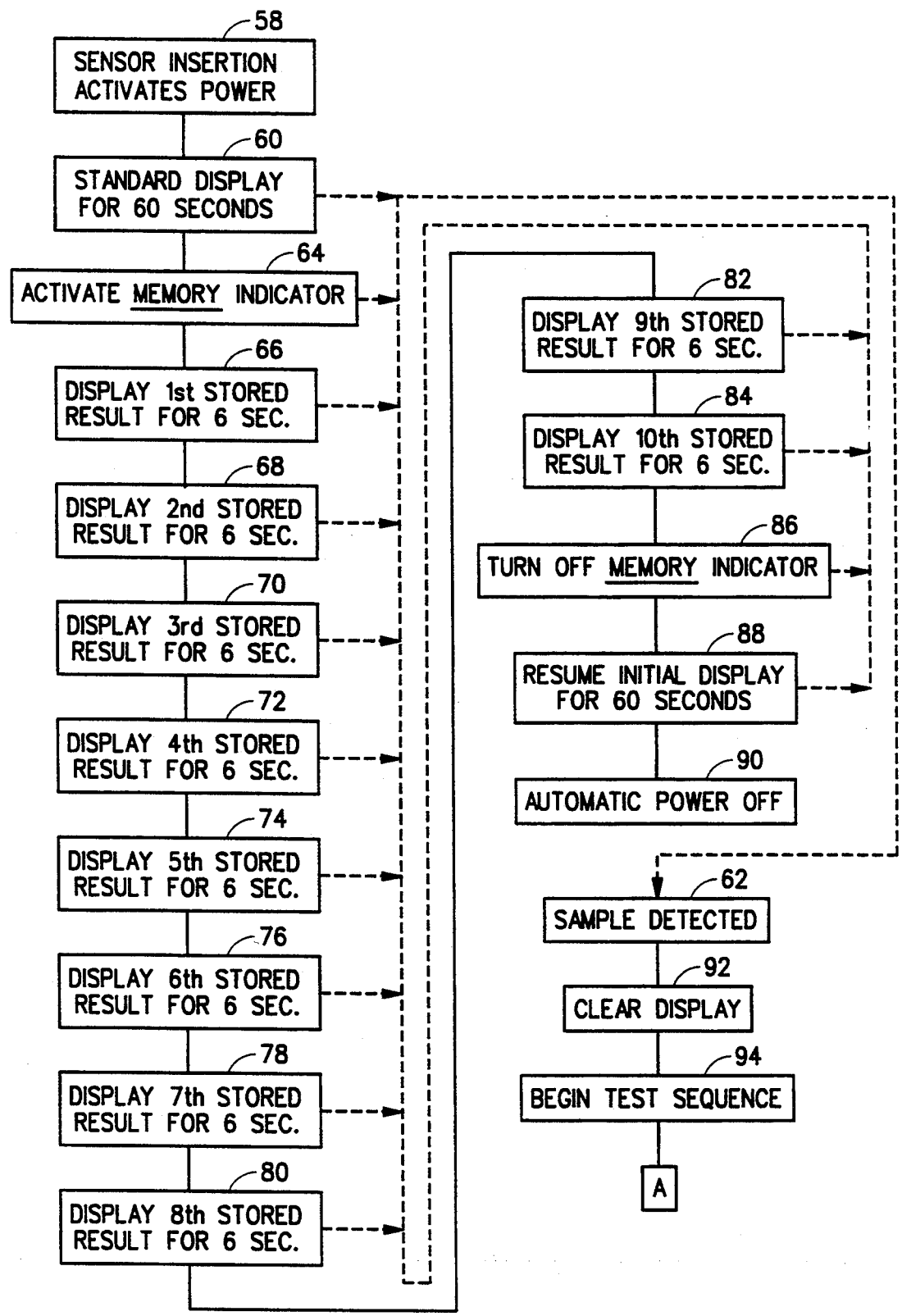
FIG. 4 illustrates a flow chart diagram detailing the retrieval of measurement results from memory by a preferred embodiment of the buttonless memory system.

As shown in FIG. 4, a user activates the meter 10 by inserting the test sensor 20 into the test slot 16 at step 58. The test sensor 20 includes a first electrode 21 and a second electrode 23 that engage corresponding electrodes (not shown) in the test slot 16. Upon activation, step 60 of the buttonless memory system displays a standard display on display 12 for 60 seconds or another selected time interval or until step 62 detects a sample for measurement. More specifically, the standard display can have the function number 24 and the last measurement test result alternating on the display 12. If the 60 seconds of step 60 passes, step 64 activates the memory indicator 14. As previously stated, the activation of the memory indicator on the display 12 signals the user that the measurement results being displayed are previously stored measurement results.

As soon as the memory indicator 14 is activated, steps 66-84 display the last 10 stored measurement results on the display 12 along with the sequence number for the measurement result and any additional information such as time and date of the measurement. If 10 measurement results are not yet present in memory, the buttonless memory system will preferably only display those measurement results currently stored in memory. Each stored measurement result is shown as being displayed for a period of time, e.g., 6 seconds, totalling 60 seconds, but this time interval, as well as other specifically shown time intervals, can be varied by the manufacturer. Moreover, the number of stored measurement results can also vary. The buttonless memory system is specifically described as storing 10 previous measurement results, but the present invention can store any predetermined number of measurement results. After the predetermined number of measurement results is stored in memory, the oldest measurement result is deleted from memory upon the storing of a new measurement result.

After the buttonless memory system cycles through steps 66-84 and displays the stored measurement results, step 86 turns off the memory indicator 14 of the display 12, and step 88 resumes displaying the standard display for 60 seconds or any appropriate time interval. After step 88, if a sample has not been detected, step 90 automatically deactivates the blood/glucose meter 10. If the blood/glucose meter 10 detects a sample during any of the steps 60-88, the buttonless memory system proceeds to clear the display 12 at step 92 and initiates the test sequence on the sample for measurement at step 94.

Figure 5:
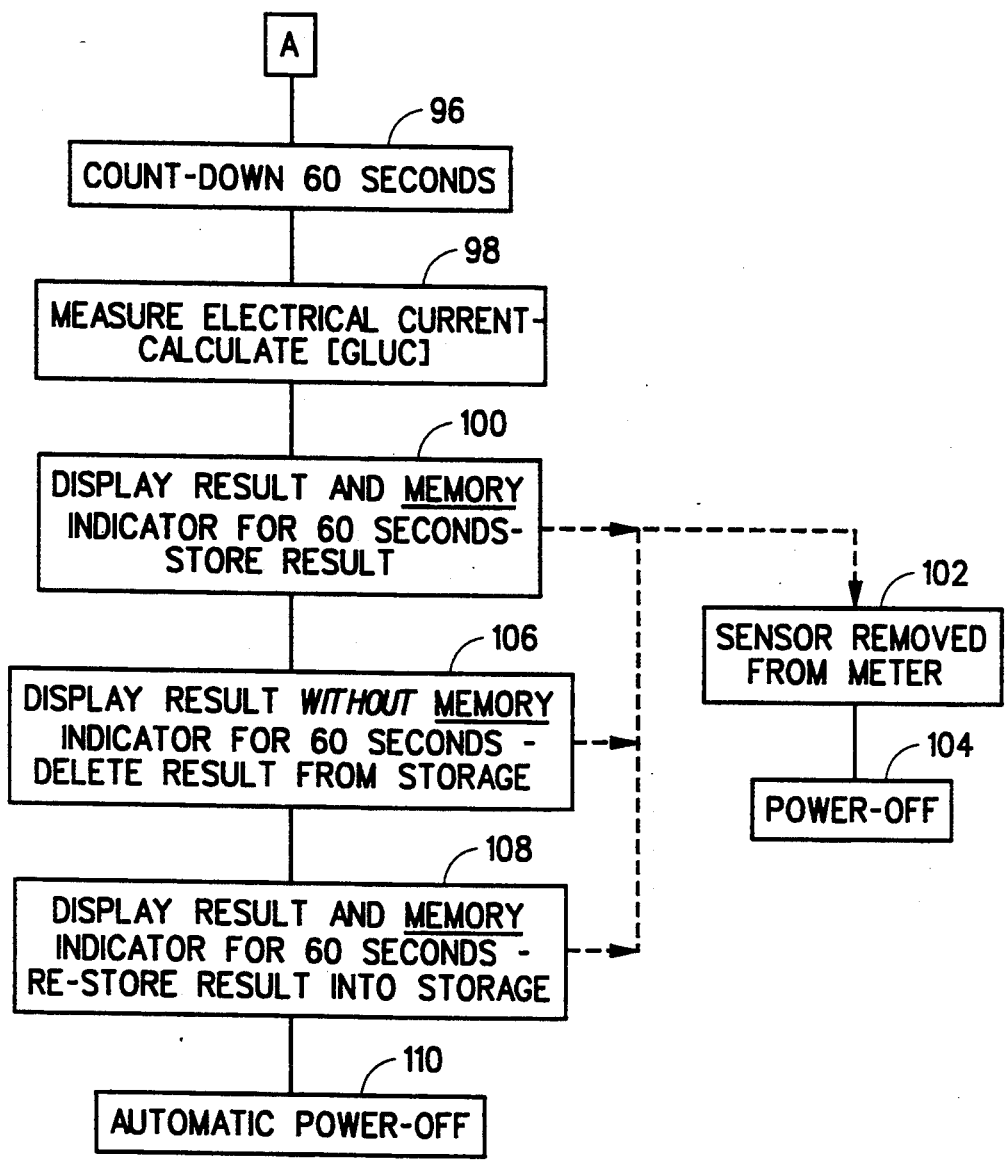
FIG. 5 illustrates a flow chart diagram detailing the storage of measurement results into memory by a preferred embodiment of the buttonless memory system.

After the blood/glucose meter 10 detects the sample for measurement at step 94, FIG. 5 shows the operation of the meter 10 using the buttonless memory system. Step 96 counts down 60 seconds on the display 12, and, during those 60 seconds, the meter 10 calculates the glucose level in the blood sample using electrode sensor technology at step 98. At step 100, the buttonless memory system displays the result of the blood/glucose calculations and activates the memory indicator 14 on the display 12 for 60 seconds or any appropriate time interval or until the test sensor 20 is removed from the test slot 16 at step 102 which deactivates the meter 10 at step 104. The buttonless memory system automatically stores the result in memory, and the memory indicator 14 signals the user that the current measurement result is stored in memory at step 100. Thus, if the user wishes to store the measurement result in memory, the user simply deactivates the meter 10 by removing the test sensor 20 when the memory indicator 14 is on.

If the user does not remove the test sensor 20 from the test slot 16 and 60 seconds pass or any appropriate time interval, step 106 of the buttonless memory system displays the result on the display 12 without the memory indicator 14 for 60 seconds or any appropriate time interval. The absence of the memory indicator 14 signals the user that if the user removes the test sensor 20 from the test slot 16 and deactivates the meter 10, the displayed result will be deleted from memory. Commonly, a user will not want to store a measurement result in memory. For example, the user can test a control solution to determine whether the blood/glucose meter is operating properly. The user, however, does not want to store the measurement result for the control solution because that result does not reflect a measurement result for an actual blood sample. Therefore, if the user removes the test sensor 20, deactivating the meter 10, during the 60 seconds that the result is on the display 12 without the memory indicator 14, the buttonless memory system does not store the result in memory.

If the 60 seconds of step 106 pass, the user still has another opportunity to store the measurement result. Step 108 continues displaying the measurement result and activates the memory indicator 14 for 60 more seconds or any appropriate time interval. Once again, the memory indicator 14 signals the user that the measurement result is stored in memory, and the user can safely deactivate the meter 10. After 60 seconds or the appropriate time interval, if the user has not deactivated the meter 10, step 110 automatically turns off the meter 10.

The present invention has been specifically described as being used with a portable blood/glucose meter using electrode sensor technology. The present invention, however, can be used with other portable electrical measurement devices with memory storage and display capabilities. The present invention is a buttonless memory system or a simplified memory management scheme for these portable measurement devices. These portable measurement devices range from an electronic measurement device using a processor and adequate memory to implement the buttonless memory system to a measurement device where the buttonless memory system is hard-wired into the measurement device.

The operation of the buttonless memory system is specifically described, but the present invention encompasses deviations from the above description of features, timing and functions. The buttonless memory system retrieves and stores the measurement results for the user without requiring any button pressing or switch switching from the user. The user simply deactivates or pulls out the test sensor from the portable measurement device during the proper time period corresponding to the desired memory management feature. The user simply waits for an indication of the desired memory feature at the appropriate time. The buttonless memory system encompasses performing these memory management features at different times during the operation of the measurement device 10 from those times specifically described above. For example, instead of displaying a 60 second countdown during the actual analysis of a sample, the measurement device 10 could be designed to retrieve and display previous measurement results at that time. Thus, the buttonless memory system can perform various memory management features during the operation of the measurement device 10 at different times than those specifically disclosed.

Furthermore, the buttonless memory system can include memory management features in addition to the features of the retrieval of previous measurement results from memory, storage of a current measurement result in memory and deletion of a current measurement result from memory, such as deleting previous measurement results from memory or restoring deleted measurement results to memory.

Additionally, the manner of activating these memory management features is described as depending upon visual prompts and timing. The buttonless memory system includes various methods of informing the user that a particular function is to be performed. For example, the user could perform the deletion of previous measurement results by deactivating the measurement device 10 (e.g., by removing the test sensor 20) when the memory indicator 14 or display 12 "blinks" for a period of time while the buttonless memory system cycles through each of the previous measurement results in memory.

Alternatively, the buttonless memory system can employ a different memory indicator for each memory function. In this way, the buttonless memory system further simplifies its memory management scheme and also permits the user to perform different memory functions without confusion at various times following the activation of the measurement device. For example, if a memory indicator only represents the retrieval of previous measurement results from memory, this retrieval function could be automatically performed at any time without confusion, not just after the measurement device is activated. Additionally, in FIG. 1, the memory indicator 14 is shown on display 12, but the memory indicator can take many forms, such as an LED. Indeed, the display 12 can indicate the activation of a memory feature using a memory message on the display 12 without a separate memory indicator 14 at all.

In another embodiment of the buttonless memory system, the user can activate a desired memory management feature by manipulating the test sensor 20 in a distinct manner. For example, the user can delete a stored measurement result from memory by removing the test sensor 20 from the test slot 16 and immediately re-inserting the test sensor 20 into the test slot 16 while that measurement result is being displayed. In this case, the removal of the test sensor 20 does not completely deactivate the measurement device 10.

In yet another embodiment of the present invention, the buttonless memory system includes voice-activated circuitry. This voice-activated circuitry conventionally detects and recognizes certain verbal commands. The buttonless memory system can employ voice-activation to immediately activate a certain memory management feature. For example, the buttonless memory system can immediately retrieve previous measurement results from memory and display them in response to a spoken "memory" command at any time. A verbal "run test" command can commence a test sequence on a test sensor 20. Similarly, a "store" command results in the storing of the measurement result in memory, and "delete" removes the measurement result from memory at any time.

The invention has also been described in terms of making quantitative or qualitative measurements of glucose in whole blood or plasma. It will be understood that, depending on the measurement device, other analytes such as cholesterol can be measured. Indeed, the sample employed does not even have to be whole blood or plasma. Any body fluid or synthetic solution can be used.

Thus, the buttonless memory system of the present invention and many of its attendant advantages will be understood from the foregoing description and various modifications can be made in the form, construction and arrangement of the parts and steps thereof without departing from the spirit and scope of the invention or sacrificing all of its material advantages, the form described above being merely a preferred or exemplary embodiment thereof.

I claim:

1. A buttonless memory system for an electrical measurement device, said measurement device including a measurement mechanism for analyzing a sample, said measurement device further including a display for displaying a result derived from said analysis, said measurement device being characterized as a measurement device for analyzing liquid samples, comprising:

a memory for storing said result along with previous results stored in said memory; and a processor coupled to said measurement mechanism, said processor controlling said analysis of said sample by said measurement mechanism and calculating said result from said analysis, said processor further coupled to said display and said memory, said processor displaying said previous results and indicating during a first time period that said display is displaying said previous results stored in said memory, said processor storing said result for a second time period after calculating said result such that said result remains stored in said memory if said measurement device is turned off during said second time period, said processor deleting said result from said memory if said measurement device is not turned off during said second time period.

2. The buttonless memory system of claim 1 wherein said electrical measurement device is a portable blood/glucose meter obtaining a glucose level in said sample as said result.

3. The buttonless memory of claim 2 wherein said blood/glucose meter utilizes electrode sensor technology.

4. The buttonless memory system of claim 1 wherein said processor indicating on said display the retrieval of said previous results from said memory, the storage of said result in said memory, and the deletion of said result from said memory.

5. The buttonless memory system of claim 1 further comprising a memory indicator coupled to said processor for indicating the retrieval of said previous results from said memory, the storage of said result in said memory and the deletion of said result from said memory.

6. The buttonless memory system of claim 5 wherein said memory indicator is an LED.

7. The buttonless memory system of claim 5 or 6 further comprising a plurality of memory indicators, each of said plurality of memory indicators for indicating a different memory management feature.

8. The buttonless memory system of claim 1 wherein said memory includes a ROM for storing operation instructions and a RAM for storing said measurement results and any additional measurement information.

9. The buttonless memory system of claim 1 further comprising voice-activated circuitry coupled to said processor, said voice-activated circuitry responsive to voice commands, each voice command corresponding to a memory management feature and signalling said processor to perform said memory management feature corresponding to said voice command.

10. A method for performing memory management features on a memory of an electrical measurement device requiring minimal user interaction, said electrical measurement device being characterized as a measurement device for analyzing a liquid sample, obtaining a measurement result from said sample and displaying said result, comprising the steps of:

indicating to the user that previous measurement results stored in said memory are being displayed;

retrieving and displaying said previous measurement results stored in said memory for a first time period;

storing said measurement result for said sample in said memory after obtaining said measurement result from said electrical measurement device for a second time period such that said result remains stored in said memory if said electrical measurement device is turned off during said second time period; and deleting said measurement result from said memory if said electrical measurement device is not turned off during said second time period.

11. The method of claim 10 further comprising the steps of:

storing said measurement result in memory automatically after said third time period; and activating said memory indicator for a fourth time period after said third time period to signal the user that said result is stored in memory and remains stored in said memory if said electrical measurement device is turned off during said fourth time period.

12. The method of claim 10 employing a portable blood/glucose meter as said electrical measurement device to obtain a glucose level for said sample as said result.

13. The method of claim 12 employing a blood/glucose meter utilizing electrode sensor technology.

14. The method of claim 10 wherein said steps of indicating further comprise employing said display to indicate the performance of a memory management feature.

15. The method of claim 10, wherein said steps of indicating further comprise employing a memory indicator.

16. The method of claim 15 further comprising the step of employing a plurality of memory indicators, each of said plurality of memory indicators for indicating a different memory management feature.

17. The method of claim 10 further comprising the step of employing voice-activated circuitry responsive to voice commands corresponding to a memory management feature to expedite performance of the memory management feature.

* * * * *